United States Patent [19]

Schimmel et al.

[11] 4,089,846
[45] May 16, 1978

[54] POLYSALTS OF ACID-ESTER COMPOUNDS WITH HYDRAZINE OR HYDRAZIDES AND METHOD OF PREPARING HETEROCYCLIC POLYMERS FROM SAID POLYSALTS

[75] Inventors: Karl F. Schimmel, Verona; Marco Wismer, Gibsonia, both of Pa.

[73] Assignee: PPG Industries, Inc., Pittsburgh, Pa.

[21] Appl. No.: 628,611

[22] Filed: Nov. 4, 1975

Related U.S. Application Data

[62] Division of Ser. No. 511,337, Oct. 2, 1974, Pat. No. 3,969,566, which is a division of Ser. No. 369,629, Jun. 13, 1973, Pat. No. 3,882,086.

[51] Int. Cl.² ............... C07C 109/04; C07C 109/087; C07C 109/10; C08G 73/08
[52] U.S. Cl. ..................... 260/78 TF; 260/47 CP; 260/63 R; 260/65; 260/294.8 B; 260/295 R; 260/295.5 H; 560/18; 560/70; 560/76; 560/115; 560/157

[58] Field of Search ............... 260/47 CP, 65, 78 JF, 260/471 R, 294.8 B, 295 R, 295.5 H, 468 H, 468 J, 470, 475 R, 475 FR, 475 N, 485 J, 473 R, 468 G, 63 R

[56] References Cited

U.S. PATENT DOCUMENTS 3,360,502  12/1967  Loncrini .................... 260/78

FOREIGN PATENT DOCUMENTS 376,88R  5/1970  Japan ...................... 260/78

OTHER PUBLICATIONS

Korshak et al., Preparation of Polymers from Pyromelitic Dianhydride and Hydrazine, C.A. vol. 70, 1969, 68816w.

*Primary Examiner*—Lester L. Lee
*Attorney, Agent, or Firm*—John E. Curley

[57] ABSTRACT

Novel polymers formed from the reaction of tricarboxylic anhydrides and hydrazines or hydrazides which may be cross-linkable by further reaction with a hydrazine or hydrazide are disclosed.

3 Claims, No Drawings

POLYSALTS OF ACID-ESTER COMPOUNDS WITH HYDRAZINE OR HYDRAZIDES AND METHOD OF PREPARING HETEROCYCLIC POLYMERS FROM SAID POLYSALTS

This is a division of application Ser. No. 511,337, filed Oct. 2, 1974 now U.S. Pat. No. 3,969,566, which is a division of U.S. patent application Ser. No. 369,629, filed June 13, 1973, now U.S. Pat. No. 3,882,086, issued May 6, 1975.

DESCRIPTION OF INVENTION

Briefly this invention comprises novel polymers preferably formed from the reaction of a tricarboxylic anhydride and a monofunctional alcohol to form an ester-acid of the formula:

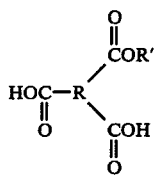
(I)

which is subsequently reacted with a hydrazine or hydrazide to form a polysalt having the structural formula:

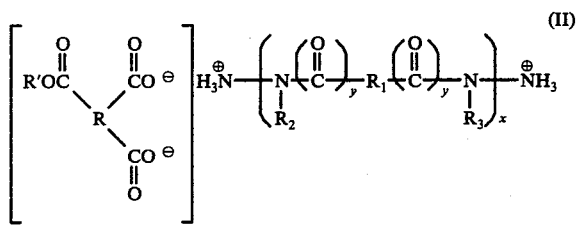
(II)

the above polysalt is then heated to form a compound of the structural formula:

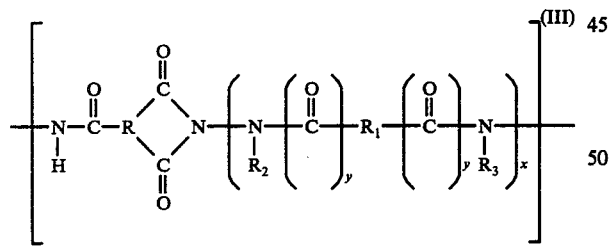
(III)

the above (III), when R is aldehyde ketone, aliphatic chlorine, bromine or iodine functional, can be further reacted with a hydrazine or hydrazide to form a crosslinked network. By aliphatic chlorine, bromine or iodine functional is meant any aliphatic radical having a chlorine, bromine or iodine atom or atoms and includes aromatics having aliphatic groups containing chlorine, bromine, or iodine atoms thereon connected to the aromatic ring.

In the above formulae R is a trivalent organic radical having at least 2 carbon atoms. Examples of trivalent organic radicals are, but not limited to the aromatic trivalent radicals of the structure:

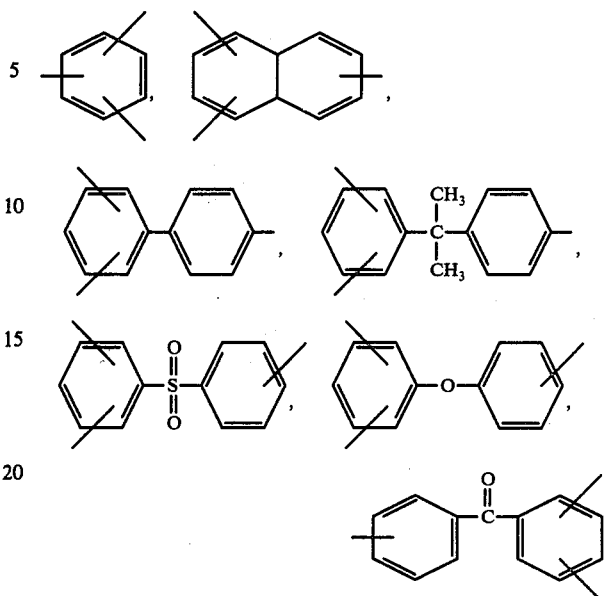

and the like, and the aliphatic and cycloaliphatic trivalent organic radicals, such as

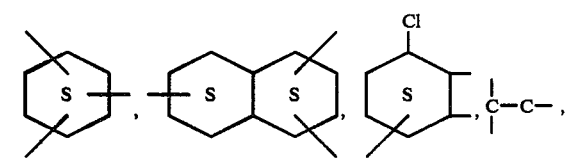

and the like, $R_1$ is a divalent organic having at least 2 carbon atoms; examples of said divalent organic radicals are, but not limited to, the aromatic divalent organic radicals, such as:

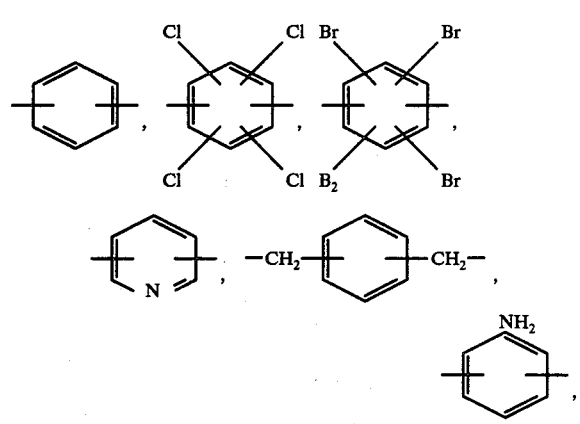

and the like, and the divalent organic aliphatic radicals, such as

wherein $n$ is 2 to 34,

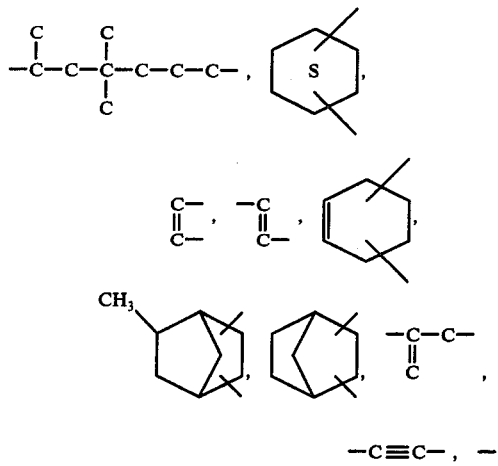

and the like.

R' is a monovalent alkyl cycloalkyl or alkenyl radical having 1 to 20 carbon atoms.

$R_2$ and $R_3$ are selected from the group consisting of monovalent alkyl, aryl, aralkyl, cycloalkyl, heterocycloalkyl and hydrogen radicals and isomers thereof, and $x$ and $y$ are either 0 or 1.

Any hydrazine or dihydrazide is suitable for cross-linking the compounds of formula III (when R is ketone, aldehyde, aliphatic chlorine, bromine or iodine containing), provided the hydrazine or dihydrazide has two terminal — $NH_2$ groups, examples of hydrazines useful for cross-linking are, but not limited to; hydrazine, 1,2-ethylene dihydrazine, p-phenylene dihydrazine, alpha, alpha'-diethyl-m-phenylene dihydrazine, and the like; examples of hydrazides are, but not limited to, succinoyl dihydrazide, adipoyl dihydrazide, isophthaloyl dihydrazide, terephthaloyl dihydrazide, pyridine-2,4-dicarbonyl dihydrazide and the like.

The cross-linking reaction is accomplished, when R is aldehyde or ketone functional, by reacting the carbonyl containing polymer with the hydrazine or hydrazide to form a cross-linking bridge of the structure

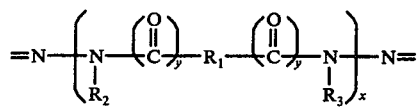

wherein $R_1$, $R_2$, $R_3$, $x$ and $y$ are of the structures and values as previously described.

The cross-linking reaction is effected by the ketone or aldehyde carbonyl reacting, i.e., condensing, with the terminal — $NH_2$ group of the hydrazine or hydrazide employed to produce the cross-linked polymer and the water of condensation as a by-product. When the functionality of R is aliphatic chlorine, bromine or iodine, the terminal — $NH_2$ groups of the hydrazine or hydrazide react with the halogen bearing carbon atom to produce a cross-linking bridge of the structural formula

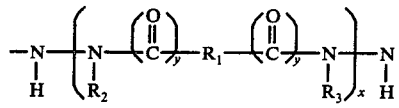

wherein $R_1$, $R_2$, $R_3$, $x$ and $y$ are of the structures and values as previously described.

Hence, the physical properties of the final polymeric material can be adjusted by the degree of cross-linking of the polymer. Further, the degree of cross-linking can be varied by the amount of ketone, aldehyde, aliphatic chlorine, bromine or iodine functional tricarboxylic anhydride used in the synthesis of the polymer. The degree of cross-linking can also be varied by the stoichiometric amount of the hydrazine or the hydrazide used in the synthesis of the polymer. Therefore, a wide range of chemical and physical properties of the cross-linked polymer can be achieved, making the cross-linked polymers of the instant invention adaptable for a plurality of uses.

The polymers of the instant invention can be further modified by substituting a portion of the hydrazine or dihydrazide in formula II with a diamine, thereby introducing polyimide groups into the polymer chain. Suitable diamines for the aforementioned purpose are, but not limited to, ethylene diamine, 4,4'diaminodiphenyl propane, 4,4'diaminodiphenyl methane, benzidine, 3,3'-dichloro-benzidine; 4-4'diaminodiphenyl sulfide; 3,3'diaminodiphenyl sulfone; 1,5-diaminonapthalene, meta-phenylenediamine, para-phenylene-diamine; 3,3'dimethoxy benzidine and the like.

In addition to the modification of the polymers of the instant invention by means of substitution of a diamine for the hydrazine or dihydrazide, the polymers can be modified by substituting a portion of the tricarboxylic dianhydride with a tetracarboxylic dianhydride for the purpose of providing additional

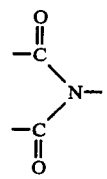

groups along the polymer cahin. These tetracarboxylic - hydrazine or hydrazide reaction products being more fully described in copending application Ser. No. 369,628, filed June 13, 1973, now abandoned.

The preferred method of forming the polymers of the instant invention comprises: admixing 1 mole of tricarboxylic dianhydride with a suitable solvent, adding 1 mole of monofunctional alcohol to form the acid — ester of formula I, subsequently adding the hydrazine or dihydrazide (in a sufficient amount to form either the cross-linked or noncross-linked polymer on heating) to produce the polysalt of formula II. At this stage the solution can be further reduced in polyslat concentration by the addition of an aqueous nitrogenous base solution consisting of aqueous ammonia or amine solution or additional organic solvent. The polysalt, either aqueous or non-aqueous, can be coated on a substrate such as glass, glass fibers, metal, wood or the like and heated to a temperature of about 200° C. to form either the compound of formula III or the cross-linked version thereof.

Another method of forming the polymers of the instant invention comprises admixing 1 mole of the tricarboxylic dianhydride with the monofunctional alcohol to form the ester — diacid of the tricarboxylic acid, and subsequently adding the hydrazine or dihydrazide (in an amount sufficient to form either the cross-linked or noncross-linked polymer on heating) and subsequently heating the mixture to above 100° C. to form a polysalt having the structural formula:

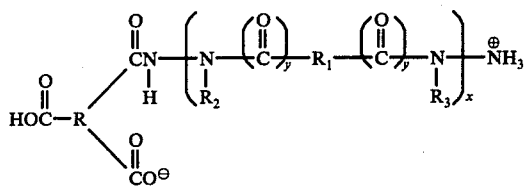

The above method has been characterized by specific molar amounts of reactants, however different molar amounts may be used providing the molar ratios of the reactants remain the same.

The latter method of forming the polymers of the instant invention is desired in order that the hydrazine or hydrazide is chemically bonded to the trifunctional R group, hence, eliminating the possibility of vaporization of the hydrazine or hydrazide on subsequent heating causing a disproportionation of the stoichiometry of the reactants.

Suitable solvents for admixing with the tricarboxylic anhydride are those having a high degree of polarity. Examples of such solvents are N-N-dimethyl acetamide; N,N-dimethyl formamide; dimethyl sulfoxide; N-methyl pyrrole, methyl isobutyl ketone, ethyl alcohol and the like.

Transesterification catalysts can be used to aid in the conversion of the polysalt to the polymer of formula III. Examples of such transesterification catalysts are, but not limited to, oxalic acid, dimethyl terephthalate, dibutyl sebacate, butyl stannoic acid and the like.

Coating techniques known to those skilled in the art can be used for depositing the polysalts of formula II on the desired substrate. For example, when the compound of formula III is to be used as a binder for glass fibers, application can be achieved by dipping a mat of glass fibers, or glass fiber paper into an aqueous ammonia polysalt (formula II) solution and allowing the glass fiber material to soak into said glass fibers (approximately 1 to 30 seconds). After soaking, the glass fiber material is permitted to drip dry and then is subsequently baked at approximately 250° to 300° F. for about 30 to 60 minutes. Thus, fiber glass paper or fiber glass mat is produced which may tolerate temperatures of up to greater than 500° F. without substantial loss of strength or integrity.

The polymers of the instant invention can be used as binders for fibers such as cotton, hemp, wool, hair, silk, rayon, nylon, Orlon ®, saran, Ardil ®, and the like in addition to glass fibers to impart temperature resistance and strength to the aforementioned fibers.

Fiber reinforced laminates and castings and nonreinforced castings can be produced by the polymers of the instant invention where certain chemical and physical properties are desired.

Further, coated metallic conductive wire such as copper or zinc, can be produced by dipping the selected wire into the polysalt (formula II) solution, (the solution being aqueous or nonaqueous) and subsequently heating the polysalt coated wire to a temperature adequate to convert the polysalt to the polymer of formula III or a cross-linked version thereof. Wire coated by polymers having the repeating structural unit of (formula III) or the cross-linked version thereof may withstand service temperatures of 400° F. without any observable degeneration of the polymer coating; thus, an insulated wire is produced capable of withstanding elevated service temperatures. The coating thickness on the surface of the wire can be adjusted by the viscosity of the polysalt solution. A low (25 centipoises at 20° C.) viscosity polysalt solution would produce a thin coating ($\approx$10 microns) and a high viscosity ($\approx$1000 centipoises at 20° C.) polysalt solution would produce a thick coating (about 30 microns).

Also, flat or contoured substrates such as the cellulosics including wood, paper and the like; glass, metal and the like can be coated with the polysalt of formula II by spraying the low viscosity polysalt solution by conventional spraying techniques; by applying the polysalt solution with a standard paint brush, by depositing the polysalt solution by any other conventional coating techniques; the technique selected being contingent on the substrate and film thickness desired.

The polysalt can be pigmented with pigments such as titanium dioxide, zinc oxide, calcium carbonate, lithopone, phthalocynine blue, carbon black, iron oxide or the like to impart color to the coating or with silica, clay, talc and the like to impart the desired film and solution properties to the polysalt and subsequently formed polymer. The polysalt which is deposited on a substrate may be used as a coating in itself, due to the hard, cohesive properties of the polysalt after the solvent and/or water and ammonia evaporate, or the polysalt can be heated to form the polymer of formula III or the cross-linked version thereof. If fire retardant coating properties are desired, the polysalt film itself is the desired coating, however, the polymer of formula III or the cross-linked version thereof also imparts fire retardant characteristics.

In addition, adhesive compositions can be formed by the polymers of the instant invention in that the polymer structure can be adapted to have bonding characteristics to metal, glass, mica, asbestos, wood, paper and like substrates.

The invention will be more clearly illustrated by the examples below; however, these examples which describe specific embodiments should not be construed to limit the invention in any way.

EXAMPLE I

Solution A: To a two liter round bottom flask equipped with a water cooled reflux condenser, a thermometer, a heating mantle and a mechanical agitator was charged 500 grams of trimellitic anhydride (1,2,4 benzenetricarboxylic acid monoanhydride) and 500 grams of ethyl alcohol. The mixture was heated to reflux and refluxed for 1 hour and then cooled to room temperature. The mixture did not form a solution. 250 grams of the above mixture was placed in a five liter beaker and manually agitated at ambient temperature with 500 grams of water and 500 grams of ethyl alcohol until a clear solution was formed.

Solution B: 52 grams of 85% hydrazine hydrate was added to 350 grams of water at ambient temperature and manually agitated until homogeneous.

Polysalt formation and binder solution: Solution B was added to Solution A with manual agitation at ambient temperature and stirred until homogeneous. Subsequently, 1152 grams of water was added to the above solution at ambient temperature with agitation and a homogeneous solution resulted.

Application to glass fiber paper: Glass fiber paper was dipped in the binder solution for about 3 seconds and then the glass fiber paper (100% glass fibers) with the binder solution thereon was heated to 300° F. for 1 hour in a forced air oven. Microscopic examination of the coated glass fiber paper showed a uniform coating of binder on the glass fibers. Two samples of glass fiber paper coated as above described exhibited good strength and after 4 hours of subjecting the above coated glass fiber paper samples to 600° F., the polymer weight loss of each sample was 16.41% ± 0.61%.

EXAMPLE II

A binder solution was formed in accordance with the components and procedure of Example I, but the additional 1152 grams of water was not added after the polysalt was formed.

This binder solution was applied to the glass fiber paper (100% glass fibers) by supporting said paper on a Buchner funnel having the same interior dimensions and configuration as the glass fiber paper, and pouring the binder solution onto the glass fiber paper while applying a vacuum to the surface of the glass fiber paper opposite the surface of initial contact with the binder solution. Two samples of the glass fiber paper coated as above described exhibited good strength and after subjecting the above coated glass fiber paper samples to 600° F. for 4 hours, the polymer weight loss of each sample was 11.64% ± 0.20%.

EXAMPLE III

Preparation of Terephthaloyl Dihydrazide: To a two liter round bottom flask equipped with a water cooled reflux condenser, a thermometer, a heating mantle and a mechanical agitator was charged 388 grams of dimethyl terephthalate, 473 milliliters of 85% hydrazine hydrate and 1 liter of ethanol, the above mixture was held at reflux for 12 hours and allowed to cool. After cooling to ambient temperature, the crystalline terephthaloyl dihydrazide was filtered and washed with denatured alcohol and subsequently vacuum dried.

Solution A: To a two liter round bottom flask equipped with a water cooled reflux condenser, a thermometer, a heating mantle and a mechanical stirrer was charged 192 grams of trimellitic anhydride and 350 grams of ethyl alcohol. The mixture was heated and refluxed for 1 hour and then cooled to room temperature. The mixture formed a homogeneous solution.

Solution B: 213 grams of terephthaloyl dihydrazide was mixed, employing manual agitation, in a three liter beaker with 500 grams of pyrollidone and 200 grams of water at ambient temperature until a homogeneous solution was formed.

Polysalt formation and binder solution: Solution A was added to Solution B with manual agitation at ambient temperature.

The above binder solution was coated on 100% glass fibers in accordance with the procedure of Example II. Two samples of the glass fibers coated as above described, exhibited good strength and after subjecting the above coated glass fiber paper samples to 600° F. for 4 hours, the polymer weight loss of each sample was about 50%.

EXAMPLE IV

Solution A: To a two liter round bottom flask equipped with a water cooled reflux condenser, a thermometer, a heating mantle and a mechanical agitator is charged 192 grams of trimellitic anhydride and 350 grams of ethyl alcohol. This mixture is heated to reflux for 1 hour and allowed to cool to room temperature.

Solution B: 40 grams of 85% hydrazine hydrate is mixed using manual agitation, with 350 grams of water at ambient temperature in a three liter beaker.

Polysalt formation: Solution A is added to Solution B at ambient temperature using manual agitation. A homogeneous solution was formed.

The above polysalt is coated on a cold rolled steel panel and allowed to air dry for 24 hours. A film produced in this manner is continuous, hard and demonstrated fire retardancy when exposed to open flame.

Although the present invention has been described with respect to specific details of certain embodiments thereof, it is not intended that such details act as limitations upon the scope of the invention except insofar as is set forth in the accompanying claims.

We claim:

1. A polysalt consisting of the repeating structural formula:

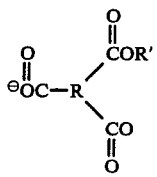

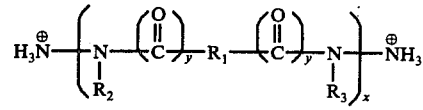

wherein R is a trivalent organic radical having at least three carbon atoms, R' is a monovalent alkyl, cyloalkyl or alkenyl radical having 1 to 20 carbon atoms, $R_1$ is a divalent organic radical selected from the group consisting essentially of alkylene, arylene and heterocyclic, $R_2$ and $R_3$ are monovalent alkyl, aryl, aralkyl, cycloalkyl or hydrogen radicals and $x$ and $y$ are either 1 or 0.

2. The polysalt of claim 1 wherein R is of the structural formula:

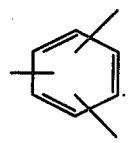

3. A method of producing a high temperature polymer comprising reacting a tricarboxylic monoanhydride with a monofunctional alcohol to form as ester-acid having the structural formula:

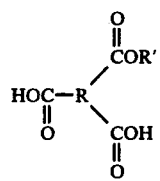

reacting said ester-acid with a member selected from the group consisting of a hydrazine and a hydrazide, thereby forming a polysalt having the structural formula:

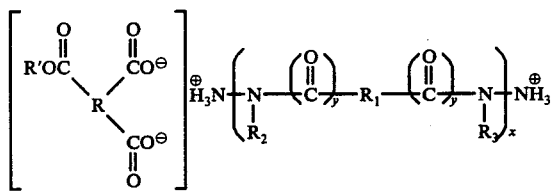

heating said polysalt to form a high temperature resistant polymer having the structural formula:

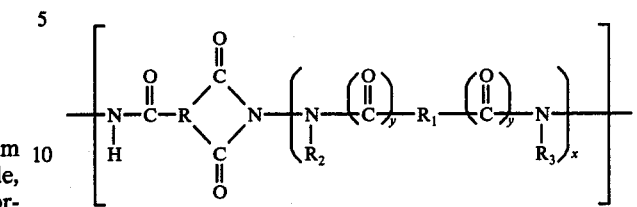

where R is a trivalent organic radical having at least two carbon atoms; $R_1$ is a divalent organic radical having at least two carbon atoms; $R_2$ and $R_3$ are monovalent alkyl, aryl, aralkyl, cycloalkyl or hydrogen radicals, $R^1$ is a monovalent alkyl, cycloalkyl or alkenyl radical having 1 to 20 carbon atoms and $x$ and $y$ are either 1 or 0.

* * * * *